（12） United States Patent
Ma

(10) Patent No.: US 9,833,153 B2
(45) Date of Patent: Dec. 5, 2017

(54) METHOD AND DEVICE FOR INFLATING A CUFF OF A NON-INVASIVE BLOOD PRESSURE MEASUREMENT APPARATUS

(75) Inventor: Sufang Ma, Shanghai (CN)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1231 days.

(21) Appl. No.: 13/576,749

(22) PCT Filed: Jan. 27, 2011

(86) PCT No.: PCT/IB2011/050353
§ 371 (c)(1),
(2), (4) Date: Aug. 2, 2012

(87) PCT Pub. No.: WO2011/101759
PCT Pub. Date: Aug. 25, 2011

(65) Prior Publication Data
US 2012/0323128 A1    Dec. 20, 2012

(30) Foreign Application Priority Data
Feb. 22, 2010 (CN) .......................... 2010 1 0113725

(51) Int. Cl.
*A61B 5/0225* (2006.01)
*A61B 5/021* (2006.01)
*A61B 5/022* (2006.01)

(52) U.S. Cl.
CPC ........ *A61B 5/0225* (2013.01); *A61B 5/02141* (2013.01); *A61B 5/02233* (2013.01); *A61B 5/02241* (2013.01)

(58) Field of Classification Search
None
See application file for complete search history.

(56) References Cited

U.S. PATENT DOCUMENTS

| 4,493,326 A | 1/1985 | Hill et al. |
| 4,969,466 A | 11/1990 | Brooks |

(Continued)

FOREIGN PATENT DOCUMENTS

| CN | 2429107 Y | 5/2001 |
| CN | 1394546 A | 2/2003 |

(Continued)

*Primary Examiner* — Jacqueline Cheng
*Assistant Examiner* — Jairo Portillo

(57) ABSTRACT

A method for inflating a cuff of a non-invasive blood pressure measurement apparatus includes obtaining a plurality of pressure values of the cuff at a plurality of time points; calculating a first inflation speed parameter on the basis of the plurality of pressure values, a plurality of target pressure values of the cuff at the plurality of time points and a plurality of inflation speed parameters corresponding to each time interval between every two adjacent time points of the plurality of time points; and inflating the cuff at a speed corresponding to the first inflation speed parameter from a last time point of the plurality of time points to a first time point after the plurality of time points. In this way, uniform cuff inflation can be achieved when the target pressure values of the cuff change uniformly, so that the over-voltage phenomenon or the condition of low-speed cuff inflation can be reduced or eliminated. By introducing the plurality of pressure values, even if there is a big error in a cuff pressure value obtained at a certain time point, it is still possible to control the cuff inflation correctly.

13 Claims, 1 Drawing Sheet

(56) References Cited

U.S. PATENT DOCUMENTS

| | | | | |
|---|---|---|---|---|
| 5,337,751 A | * | 8/1994 | Newell et al. | 600/495 |
| 5,730,139 A | * | 3/1998 | Miyazaki et al. | 600/493 |
| 6,171,254 B1 | * | 1/2001 | Skelton | 600/490 |
| 7,393,327 B2 | * | 7/2008 | Inukai et al. | 600/485 |
| 7,594,892 B2 | | 9/2009 | Cen et al. | |
| 7,846,105 B2 | | 12/2010 | Cen et al. | |
| 2007/0191770 A1 | * | 8/2007 | Moberg et al. | 604/131 |
| 2009/0124912 A1 | * | 5/2009 | McEwen et al. | 600/495 |

FOREIGN PATENT DOCUMENTS

| | | | | |
|---|---|---|---|---|
| CN | 101103908 A | | 1/2008 | |
| JP | 05146415 A | | 6/1993 | |
| JP | 2002034938 A | | 2/2002 | |
| JP | 2006-129920 | * | 8/2007 | A61B 5/0225 |
| JP | 2009279197 A | | 12/2009 | |

* cited by examiner

METHOD AND DEVICE FOR INFLATING A CUFF OF A NON-INVASIVE BLOOD PRESSURE MEASUREMENT APPARATUS

FIELD OF THE INVENTION

The invention relates to non-invasive blood pressure measurement, in particular to a method and device for inflating a cuff of a non-invasive blood pressure measurement apparatus.

BACKGROUND OF THE INVENTION

As opposed to invasive blood pressure measurement, non-invasive blood pressure measurement is a method of measuring the blood pressure of a human body indirectly. Currently, there are two categories of non-invasive blood pressure measurement methods.

One method is the auscultation measurement method on the basis of auscultation, i.e. the Korotkoff sound method. In the Korotkoff sound method, the cuff needs to be wound around the arm of the person whose blood pressure is to be measured and the stethoscope is placed at the brachial artery. Firstly, the cuff is inflated until the flow of the blood in the artery is blocked and then the cuff is deflated. A sound change will be generated during the inflation process, and the sound is referred to as Korotkoff sound. Doctors determine the blood pressure by listening to the change of the Korotkoff sound; this is referred to as the Korotkoff sound method.

The other method is the oscillometric method. Actually, the oscillometric method is an extension of the Korotkoff sound method. It blocks the flow of blood by inflating the cuff and then the cuff is deflated slowly. The blood pressure is determined by detecting the oscillation wave caused by the pulsation of the artery during the deflation process.

Currently, most of the electronic automatic blood pressure measuring devices measure the blood pressure based on the oscillometric method which has a high repeatability, consistency and accuracy and has been widely used in clinical examination.

U.S. Pat. No. 7,594,892 discloses a device for non-invasive blood pressure measurement and a safety protection method. The safety protection circuit of the measuring device is independently arranged with an auxiliary pressure measurement circuit and an auxiliary micro-processor circuit. In a normal measurement, the auxiliary micro-processor circuit periodically samples the pressure of a cuff by means of the auxiliary pressure measurement circuit and compares the sampled pressure with a nominal over-voltage protection value. If it exceeds the nominal over-voltage protection value, the auxiliary micro-processor circuit sends out a control signal to open a deflation valve until the air pressure falls below a safety pressure.

In view of the wide application of the non-invasive blood measurement, inventors of the present invention realize that the non-invasive pressure measurement has to meet certain particular requirements for particular people such as newborn babies. A newborn baby uses a relatively smaller cuff because it has relatively thinner arms. During the non-invasive blood measurement, if the cuff inflation speed is not controlled or not well controlled, there may be an over-voltage phenomenon caused by a very high inflation speed, which may make the newborn baby feel uncomfortable and thus impact the blood pressure measurement.

Furthermore, if a low cuff inflation speed is applied to avoid the over-voltage phenomenon, the measurement time may be very long due to the very low inflation speed. If the newborn baby cries because it has to lie in one position for a very long time, this may impact the accuracy of the measurement result.

Therefore, during the non-invasive blood pressure measurement of a newborn baby, it is very important to know how to control the cuff inflation. The solution disclosed by U.S. Pat. No. 7,594,892 can only solve the over-voltage problem by deflation if the pressure of the cuff exceeds the nominal over-voltage protection value. It cannot reduce or eliminate the over-voltage phenomenon during the process of inflating the cuff and it cannot solve the problem of the low cuff inflation speed.

SUMMARY OF THE INVENTION

Based on an understanding of the technical problems and prior art described above, it will be desirable to control the cuff inflation speed effectively during the non-invasive blood measurement.

To better address one or more of the above concerns, according to one aspect, a method of inflating a cuff of a non-invasive blood pressure measurement apparatus is provided. The method comprises the steps of:

obtaining a plurality of pressure values of the cuff at a plurality of time points;

calculating a first inflation speed parameter on the basis of the plurality of pressure values, a plurality of target pressure values of the cuff at the plurality of time points and a plurality of inflation speed parameters corresponding to each time interval between every two adjacent time points of the plurality of time points; and inflating the cuff at a speed corresponding to the first inflation speed parameter from a last time point of the plurality of time points to a first time point after the plurality of time points.

The basic idea is to adjust the cuff inflation speed on the basis of the actual pressure values of the cuff measured at previous time points, the target pressure values (i.e. the desired pressure values) of the cuff and corresponding inflation speeds. By setting the target pressure values to reasonable levels, the cuff inflation speed of the next time interval can be determined on the basis of the obtained cuff pressure values, the cuff target pressure values and the previous inflation speed parameters, so as to control the cuff inflation speed. Uniform cuff inflation can be achieved when the target pressure values of the cuff change uniformly, so that the over-voltage phenomenon or the condition of low-speed cuff inflation can be reduced or eliminated. In addition, by introducing the plurality of pressure values, even if there is a big error in a cuff pressure value obtained at a certain time point, it is still possible to control the cuff inflation correctly when the errors of the other pressure values of the plurality of pressure values are small.

According to another aspect, a device for inflating a cuff of a non-invasive blood pressure measurement apparatus is provided. The device comprises:

a pressure sensor for obtaining a plurality of pressure values of the cuff at a plurality of time points;

a processor for calculating a first inflation speed parameter on the basis of the plurality of pressure values, a plurality of target pressure values of the cuff at the plurality of time points and a plurality of inflation speed parameters corresponding to each time interval between every two adjacent time points of the plurality of time points; and an inflation unit for inflating the cuff at a speed corresponding to the first inflation speed parameter from a last time point of the plurality of time points to a first time point after the plurality of time points.

These and other aspects of the invention will be apparent from and elucidated with reference to the embodiments described hereinafter.

DESCRIPTION OF THE DRAWINGS

The above and other objects and features of the present invention will become more apparent from the following detailed description considered in connection with the accompanying drawings, in which.

The same reference numerals are used to denote similar parts throughout the Figures.

DETAILED DESCRIPTION

A detailed description of the present invention is given below in connection with the accompanying drawings.

Figure 1:
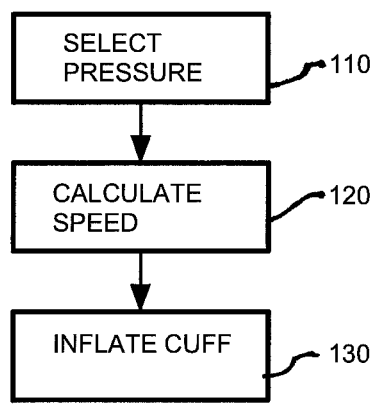
FIG. 1 depicts a flow chart of a method in accordance with an embodiment of the present invention.

FIG. 1 depicts a flow chart of a method in accordance with an embodiment of the present invention.

According to an embodiment, a method of inflating a cuff of a non-invasive blood pressure measurement apparatus is provided.

The non-invasive blood pressure measurement apparatus is configured to measure the blood pressure of a person, and it can be used independently or in cooperation with a monitoring apparatus. The non-invasive blood pressure measurement apparatus applying said method can be used for any kind of person who needs a blood pressure measurement, such as adults, children and newborn babies. The inflation method is suitable for cuffs of any dimensions (i.e. sizes). The advantages of the method are more obvious when the method is applied to the non-invasive blood pressure measurement apparatus used for measuring the blood pressure of newborn babies and/or the non-invasive blood pressure measurement apparatus having a small size cuff.

Referring to FIG. 1, the method comprises step 110 of obtaining a plurality of pressure values of the cuff at a plurality of time points.

The plurality of time points can be determined in many ways. For example, the time point when the inflation starts is set as the earliest time point of the plurality of time points, and the multiple subsequent time points of the plurality of time points are selected according to a rule that the time interval between every two adjacent time points is a predefined time period. In an embodiment, for the non-invasive blood pressure measurement of newborn babies, the predefined time period is in the range of 100 ms to 800 ms. For another example, a time point after the inflation has started for a certain period is set as the earliest time point of the plurality of time points, and the multiple subsequent time points of the plurality of time points are selected according to a predefined increasing arithmetic sequence so that the time intervals between adjacent time points change consistent with the arithmetic sequence.

The pressure values of the cuff at each time point can be obtained in many ways. For example, the pressure of the cuff is obtained using a pressure sensor. For another example, the pressure of the cuff is obtained using a primary pressure sensor and an auxiliary pressure sensor.

The method further comprises step 120 of calculating a first inflation speed parameter on the basis of the plurality of pressure values, a plurality of target pressure values of the cuff at the plurality of time points and a plurality of inflation speed parameters corresponding to each time interval between every two adjacent time points of the plurality of time points.

The plurality of target pressure values of the cuff at the plurality of time points can be determined in many ways. For example, the difference between the target pressure values at every two adjacent time points is a predefined value, such as 6 mmHg. For another example, the plurality of target pressure values is a predefined sequence. For a further example, the plurality of target pressure values is determined on the basis of the maximum pressure value required for the blood pressure measurement and the estimated total time for finishing the inflation. For example, the maximum pressure value required for the blood pressure measurement is 100 mmHg; the estimated total time for finishing the inflation is 5 seconds; if the time interval between adjacent time points is fixed at 500 milliseconds, the target pressure values corresponding to the time points from the time point when the inflation starts to the time point when the inflation finishes can be an arithmetic sequence [0, 10 mmHg, 20 mmHg, . . . , 100 mmHg]. If the plurality of time points is three time points, beginning the first second after the inflation starts, the corresponding target pressure values are 20 mmHg, 30 mmHg and 40 mmHg. The target pressure value at the time point when the inflation starts can be set in many ways, for example, it can be set to zero or to the actual pressure value of the cuff when the inflation starts.

By setting the target pressure values to reasonable levels, the cuff inflation speed for the next time interval can be determined on the basis of the obtained pressure values of the cuff, the target pressure values and the corresponding inflation speed parameter, so that the cuff inflation speed can be controlled. Uniform cuff inflation can be achieved when the target pressure values of the cuff change uniformly, so that the over-voltage phenomenon or the condition of the low speed of the cuff inflation can be reduced or eliminated.

The inflation speed parameter is the parameter relating to the inflation speed of the cuff (e.g. there is a linear relationship between the cuff inflation speed and the inflation speed parameter), and an inflation speed parameter corresponds to a corresponding inflation speed of the cuff. In an embodiment, the cuff inflation speed is controlled by means of a PWM (Pulse Width Modulation) inflation controlling method, the inflation speed parameter is the pulse duty factor and a larger pulse duty factor corresponds to a faster inflation speed. In another embodiment, the cuff inflation speed is controlled by a linear element voltage regulator circuit, the inflation speed parameter is the output voltage of the linear element voltage regulator circuit and a higher output voltage corresponds to a faster inflation speed.

The cuff inflation speed can be effectively adjusted on the basis of the measured actual pressure values of the cuff at the previous time points, the target pressure values of the cuff and the previous inflation speed parameters. Furthermore, by introducing the plurality of pressure values at the plurality of time points, even if there is a big error in a cuff pressure value obtained at a certain time point, it is still possible to control the cuff inflation correctly when the errors of the other pressure values are small.

The method further comprises step 130 of inflating the cuff at a speed corresponding to the first inflation speed parameter from a last time point of the plurality of time points to a first time point after the plurality of time points.

The first time point after the plurality of time points can be determined in many ways, for example, by determining the first time point using a method similar to the method of determining the plurality of time points. In an embodiment, if the time interval between every two adjacent time points of the plurality of time points is a predefined time period, the time interval between the last time point of the plurality of time points and said first time point is also the predefined time period.

Based on an inflation speed parameter corresponding to a time interval (i.e. a time period, such as a time period from the last time point of the plurality of time points to a first time point after the plurality of time points), the cuff can be inflated at a speed corresponding to said inflation speed parameter by an inflation unit, such as an inflation unit comprising an inflation circuit and an inflator. For example, when the cuff inflation speed is controlled by means of the PWM inflation controlling method and the inflation speed parameter is the pulse duty factor, which is 30% for a time period, then the inflation circuit generates a pulse whose pulse duty factor is 30% to control the inflator to inflate the cuff. For another example, when the cuff inflation speed is controlled by the linear element voltage regulator circuit and the inflation speed parameter is the driving voltage, which is 4V for a time period, then the inflation circuit generates a driving voltage of 4V to drive the inflator to inflate the cuff.

Step 120 described above can be implemented in many ways.

In an embodiment, step 120 can be implemented according to equation 1.

$$S = \sum_{i=1}^{n-1} \frac{PM_{i+1} - PM_i}{P_{i+1} - P_i} \times S_i \times K_i \qquad \text{Equation 1}$$

In equation 1, S is the first inflation speed parameter, n is the total number of time points of the plurality of time points, $PM_i$ is the target pressure value of the cuff at time point i of the plurality of time points, $P_i$ is the pressure value of the cuff at time point i of the plurality of time points, $S_i$ is the inflation speed parameter corresponding to the time interval between time point i and time point i+1, and $K_i$ is a weighting factor.

The ratio between the variation value of the target pressure values of each time interval and the variation value of the actual pressure values is applied as a factor for determining the inflation speed for the next time interval, so that the change of the cuff pressure value can be traced in a better way to control the speed of the cuff inflation.

The weighting factors can be determined in many ways. For example, the weighting factors are determined according to a rule that the weighting factors corresponding to the time points which are relatively closer to the first time point are relatively larger, i.e. $K_{i+1} \geq K_i$. For another example, the weighting factors are determined according to a rule that the sum of the weighting factors is a fixed value, such as $$\sum_{i=1}^{n-1} K_i = 1.$$

Optionally, whether the inflation speed parameter corresponding to a time interval (i.e. a time period) is used for calculating the first inflation speed is determined by setting the weighting factor corresponding to said time interval to zero or non-zero.

How to calculate the first inflation speed parameter by means of equation 1 is explained in detail in the following examples.

For example, at time point $t_1$, the obtained cuff pressure value is $P_1$, the corresponding target pressure value is $PM_1$; at time point $t_2$, the obtained cuff pressure value is $P_2$, the corresponding target pressure value is $PM_2$; at time point $t_3$, the obtained cuff pressure value is $P_3$, the corresponding target pressure value is $PM_3$; for the time interval from time point $t_1$ to time point $t_2$, the corresponding inflation speed parameter is $S_1$, the corresponding weighting factor is 1/2; for the time interval from time point $t_2$ to time point $t_3$, the corresponding inflation speed parameter is $S_2$ the corresponding weighting factor is 1/2; and then the inflation speed parameter $S_3$ corresponding to the time interval from time point $t_3$ to time point $t_4$ can be calculated by means of equation 2.

$$S_3 = \frac{PM_3 - PM_2}{P_3 - P_2} \times S_2 \times \frac{1}{2} + \frac{PM_2 - PM_1}{P_2 - P_1} \times S_1 \times \frac{1}{2} \qquad \text{Equation 2}$$

In the above example, if the weighting factor is zero for the time interval from time point $t_1$ to time point $t_2$ and the weighting factor is one for the time interval from time point $t_2$ to time point $t_3$, then the inflation speed parameter $S_3$ corresponding to the time interval from time point $t_3$ to time point $t_4$ can be calculated by means of equation 3.

$$S_3 = \frac{PM_3 - PM_2}{P_3 - P_2} \times S_2 \qquad \text{Equation 3}$$

For another example, at time point $t_1$, the obtained cuff pressure value is $P_1$, the corresponding target pressure value is $PM_1$; at time point $t_2$, the obtained cuff pressure value is $P_2$, the corresponding target pressure value is $PM_2$; at time point t3, the obtained cuff pressure value is $P_3$, the corresponding target pressure value is $PM_3$; at time point $t_4$, the obtained cuff pressure value is $P_4$, the corresponding target pressure value is $PM_4$; for the time interval from time point $t_1$ to time point $t_2$, the corresponding inflation speed parameter is $S_1$, the corresponding weighting factor is 1/6; for the time interval from time point $t_2$ to time point $t_3$, the corresponding inflation speed parameter is $S_2$, the corresponding weighting factor is 1/3; for the time interval from time point $t_3$ to time point $t_4$, the corresponding inflation speed parameter is $S_3$, the corresponding weighting factor is 1/2; and then the inflation speed parameter $S_4$ corresponding to the time interval from time point $t_4$ to time point $t_5$ can be calculated by means of equation 4.

$$S_4 = \frac{PM_4 - PM_3}{P_4 - P_3} \times S_3 \times \frac{1}{2} + \frac{PM_3 - PM_2}{P_3 - P_2} \times S_2 \times \frac{1}{3} + \frac{PM_2 - PM_1}{P_2 - P_1} \times S_1 \times \frac{1}{6} \qquad \text{Equation 4}$$

In another embodiment, step 120 is performed according to equation 5.

$$S = \sum_{i=1}^{n-1} \frac{PM_{i+1} \times PM_i}{P_{i+1} \times P_i} \times S_i \times K_i \qquad \text{Equation 5}$$

In equation 5, S is the first inflation speed parameter, n is the total number of time points of the plurality of time points, $PM_i$ is the target pressure value of the cuff at time point i of the plurality of time points, $P_i$ is the cuff pressure value at time point i of the plurality of time points, $S_i$ is the inflation speed parameter corresponding to the time interval between time point i and time point i+1, and $K_i$ is a weighting factor.

The ratio between the target pressure value and the actual pressure value of each past time interval is applied as one of the factors for determining the inflation speed for the next time interval, so that the difference between the actual pressure value and the target pressure value of the cuff can be traced in a better way to control the speed of cuff inflation.

Figure 2:
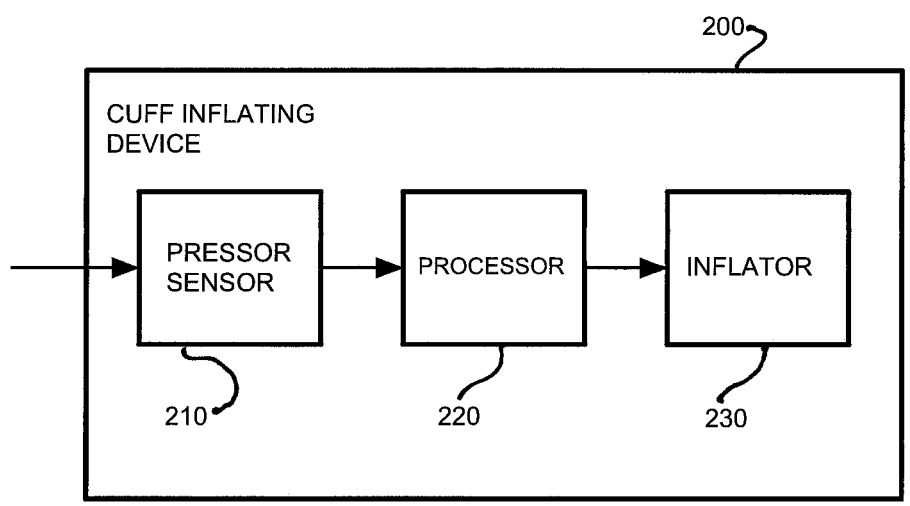
FIG. 2 depicts a schematic diagram of a device in accordance with an embodiment of the present invention.

FIG. 2 depicts a schematic paragraph of a device in accordance with an embodiment of the present invention.

According to an embodiment of another aspect of the present invention, a device 200 for inflating a cuff of a non-invasive blood pressure measurement apparatus is provided.

Referring to FIG. 2, the device 200 comprises a pressure sensor 210, a processor 220 and an inflation unit 230.

The pressure sensor 210 is for obtaining a plurality of pressure values of the cuff at a plurality of time points. The pressure sensor 210 can be implemented in many ways. For example, the pressure sensor is a high accuracy pressure sensor. For another example, the pressure sensor comprises a primary pressure sensor and an auxiliary pressure sensor.

The processor 220 is for calculating a first inflation speed parameter on the basis of the plurality of pressure values, a plurality of target pressure values of the cuff at the plurality of time points and a plurality of inflation speed parameters corresponding to each time interval between every two adjacent time points of the plurality of time points. Optionally, the time interval between every two adjacent time points is a predefined time period. The processor 220 can be implemented in many ways. For example, the processor is a high speed AMR7 inner core microcontroller. For another example, the processor comprises a primary microprocessor and an auxiliary microprocessor.

The inflation unit 230 is for inflating the cuff at a speed corresponding to the first inflation speed parameter from a last time point of the plurality of time points to a first time point after the plurality of time points. The inflation unit 230 can be implemented in many ways. For example, the inflation unit comprises a PWM circuit controlled by a single chip computer and an inflator. For another example, the inflation unit comprises a linear element voltage regulator circuit controlled by a single chip computer and an inflator.

The processor 220 can calculate the first inflation speed parameter in many ways.

In an embodiment, the processor calculates the first inflation speed parameter by means of equation 1.

In another embodiment, the processor calculates the first inflation speed parameter by means of equation 5.

It should be noted that the above-mentioned embodiments illustrate rather than limit the invention and that those skilled in the art will be able to design alternative embodiments without departing from the scope of the appended claims. The embodiments are illustrative rather than restrictive. It is intended that the invention includes all modifications and variations to the illustrated and described embodiments within the scope and spirit of the invention. In the claims, any reference signs placed between parentheses shall not be construed as limiting the claim. The word "comprising" does not exclude the presence of elements or steps not listed in a claim or in the description. The word "a" or "an" preceding an element does not exclude the presence of a plurality of such elements. In the device claims enumerating several units, several of these units can be embodied by one and the same item of hardware or software. The usage of the words first, second and third, et cetera, does not indicate any ordering. These words are to be interpreted as names.

The invention claimed is:

1. A method of inflating a cuff of a non-invasive blood pressure measurement apparatus, the method comprising the steps of:
   determining a plurality of target pressure values of the cuff for a plurality of time points;
   measuring a plurality of pressure values of the cuff at the plurality of time points;
   calculating an inflation speed parameter at one of time points (i+1), by determining a summation comprising:
   a difference between the target pressure values at said one time point (i+1) and a previous time point (i),
   a difference between the measured pressure values at said one time point (i+1) and the previous time point (i),
   a ratio of the determined difference in target pressure values to the difference in measured pressure values,
   multiplying a value of the inflation speed parameter at the previous time point (i) by the ratio and a weighting factor specific to the previous time point (i),
   wherein the summation is carried out from an initial time point (i=1) to a current time point (n−1),
   wherein the sum of the weighting factors from the initial time point (i=1) to the current time point (n−1) is equal to 1; and
   inflating the cuff at a speed corresponding to the calculated inflation speed parameter from said current time point (n−1) until a next time point (n).

2. The method as claimed in claim 1, wherein each time interval between every two adjacent time points is a predefined time period.

3. The method as claimed in claim 2, wherein the predefined time period is in a range of 100 ms to 800 ms.

4. The method as claimed in claim 1, wherein the plurality of target pressure values of the cuff is determined based on a maximum pressure value used in the blood pressure measurement and a target time to complete the inflating of the cuff.

5. The method as claimed in claim 1, wherein calculating the inflation speed parameter further includes:
   multiplying the value of the inflation speed parameter multiplied by the ratio by a weighting factor.

6. A device for inflating a cuff of a non-invasive blood pressure measurement apparatus, the device comprising:
   a pressure sensor configured to sense a plurality of pressure values of the cuff at each of a plurality of time points;
   a processor configured to:
   determine a plurality of target pressure values of the cuff for a plurality of time points;
   measure a plurality of pressure values of the cuff at the plurality of time points;
   calculate an inflation speed parameter at one of time points (i+1), by determining a summation comprising:
   p2 a difference between the target pressure values at said one time point (i+1) and a previous time point (i),
   a difference between the measured pressure values at said one time point (i+1) and the previous time point (i), a ratio of the determined difference in target pressure values to the difference in measured pressure values, multiplying a value of the inflation speed parameter at the previous time point (i) by the ratio and a weighting factor specific to the previous time point (i), wherein the summation is carried out from an initial time point (i=1) to a current time point (n−1), wherein the sum of the weighting factors from the initial time point (i=1) to the current time point (n−1) is equal to 1; and an inflation unit configured to inflate the cuff at a speed corresponding to the calculated inflation speed parameter from the current time point (n−1) until a next time point (n).

7. The device as claimed in claim 6, wherein each time interval between every two adjacent time points is a predefined time period.

8. The device as claimed in claim 7, wherein the predefined time period is in a range of 100 ms to 800 ms.

9. The device as claimed in claim 6, wherein the processor is configured to:

calculate the difference between the target pressure values at the current time point and the previous time point by subtractively combining the target pressure point for the current time point and the target pressure value for the previous time point;

calculate the difference between the sensed pressure values at the current time point and the previous time point by subtractively combining the sensed pressure point for the current time point and the sensed pressure value for the previous time point.

10. The device as claimed in claim 6, wherein the processor is configured to:

calculate the current inflation speed by multiplicatively combining the previous inflation speed parameter, the ratio, and a weighting value.

11. The device as claimed in claim 6, wherein adjacent ones of the plurality of time points are each separated by a predefined time period.

12. The device as claimed in claim 11, wherein the predefined time period is between 100 ms to 800 ms.

13. A device for inflating a cuff of a non-invasive blood pressure measurement apparatus, the device comprising:

a pressure sensor configured to sense a plurality of pressure values of the cuff at each of a plurality of time points;

a processor configured to calculate a next inflation speed parameter $S_n$, by means of the following equation:

$$S = \sum_{i=0}^{n-1} \frac{PM_{i+1} - PM_i}{P_{i+1} - P_i} \times S_i \times K_{i-1}$$

wherein n is a total number of time points of the plurality of time points, $PM_{i+1}$ is a target pressure value of the cuff at the time point i+1 of a plurality of time points, $P_{i+1}$ is the pressure value of the cuff at the time point i+1 of a plurality of time points, $S_i$ is the inflation speed parameter corresponding to the time interval between a current time point n−1 and the next time point n and $K_i$ is a weighting factor, where $K_{i+1} \geq K_1$; and $$K_{i+1} \geq K_i; \text{ and}$$

$$\sum_{i=0}^{n-1} K_i = 1; \text{ and}$$

an inflation unit configured to inflate the cuff at a speed corresponding to the calculated inflation speed parameter from the current time point (n−1) until a next time point (n).

* * * * *